(12) United States Patent
Chaniyilparampu et al.

(10) Patent No.: US 8,759,403 B2
(45) Date of Patent: Jun. 24, 2014

(54) CURCUMINOIDS AND ITS METABOLITES FOR THE APPLICATION IN ALLERGIC OCULAR/NASAL CONDITIONS

(75) Inventors: Ramchand Nanappan Chaniyilparampu, Moggapair (IN); Anitha Krishnan Nair, Moggapair (IN); Kavitha Parthasarathy, Moggapair (IN); Ganga Raju Gokaraju, Moggapair (IN); Rama Raju Gokaraju, Moggapair (IN); Kiran Bhuphatiraju, Moggapair (IN); Venkata Narashimha Siva Rama Raju Mandapati, Moggapair (IN); Nirvanashetty Somashekara, Moggapair (IN)

(73) Assignee: Laila Pharmaceutical Pvt. Ltd., Chennai, IN (US)

( * ) Notice: Subject to any disclaimer, the term of this patent is extended or adjusted under 35 U.S.C. 154(b) by 0 days.

(21) Appl. No.: 13/241,519

(22) Filed: Sep. 23, 2011

(65) Prior Publication Data

US 2012/0010297 A1  Jan. 12, 2012

Related U.S. Application Data

(63) Continuation of application No. PCT/IN2010/000016, filed on Mar. 22, 2010.

(30) Foreign Application Priority Data

Mar. 23, 2009  (IN) .............................. 646/CHE/2009

(51) Int. Cl.
*A61K 31/12* (2006.01)
(52) U.S. Cl.
USPC .......................................................... 514/678
(58) Field of Classification Search
USPC .................................................. 514/678, 826
See application file for complete search history.

(56) References Cited

U.S. PATENT DOCUMENTS

| | | | |
|---|---|---|---|
| 5,401,777 A * | 3/1995 | Ammon et al. ............... | 514/731 |
| 2004/0052877 A1 | 3/2004 | Nakayama et al. | |
| 2004/0258775 A1 | 12/2004 | Patel | |
| 2004/0266883 A1 | 12/2004 | Caplan et al. | |
| 2006/0275516 A1 | 12/2006 | Ram et al. | |
| 2007/0020197 A1 | 1/2007 | Galli et al. | |
| 2009/0263522 A1 | 10/2009 | Babish et al. | |
| 2010/0316631 A1 * | 12/2010 | Safavy ........................ | 424/133.1 |

FOREIGN PATENT DOCUMENTS

| | | | |
|---|---|---|---|
| KR | 20080020216 | * | 3/2008 |
| WO | 2006130679 A | | 12/2006 |
| WO | WO2009/121069 A2 | * | 10/2009 |
| WO | 2010070664 A | | 6/2010 |
| WO | 2010070675 A | | 6/2010 |

OTHER PUBLICATIONS

Wang et al. Enhancing stability and bioavailability of polyphenols using nanoemulsions. Abstracts of papers, 233$^{rd}$ ACS National Meeting, Mar. 25-29, 2007 AGFD-130 publisher: American Chemical Society, Washington, D.C.*

Leong et al. Minizising oil droplet size using ultrasonic emulsification. Ultrasonic Sonochemistry 15 (2009) pp. 721-727.*

International Search Report dated Sep. 14, 2010 issued for PCT/IN2010/00016.

Wang et al., Enhancing anti-inflammation activity of curcumin through O/W nanoemulsions. Food Chemistry, vol. 108, No. 2 Nov. 17, 2007, pp. 419-424.

Wang Xiaoyong et al., AGFD 130-Enhancing stability and bioavailability of polyphenols using nanoemulsions. Abstracts of Papers of American Chemical Society. vol. 233, Mar. 2007, p. 24.

Supplementary European Search Report Issued for EP10755539 dated Mar. 9, 2012.

Leong, et al., "Minimising oil droplet size using ultrasonic emulsification", Ultrasonics Sonochemistry, 16(2009) 721-727.

* cited by examiner

*Primary Examiner* — Jennifer M Kim

(74) *Attorney, Agent, or Firm* — Kramer Amado, P.C.

(57) ABSTRACT

A pharmaceutical composition for nasal administration comprising: a nanoemulsified curcumin component; a liquid medium for the curcumin component; and a pharmaceutically acceptable excipient. The curcumin component is a natural curcuminoid, a synthetic curcuminoid, a metabolite of a natural or synthetic curcuminoid, or a mixture thereof. The excipient is effective in increasing the bioavailability of the curcumin component.

24 Claims, 7 Drawing Sheets

Confocal pictures

Mice 1-Plain curcumin after 1hr of incubation

Mice 2:- Nanoemulsified curcumin after 1hr

Mice 3-Plain curcumin after 1hr

Mice 4-Nanoemulsified curcumin after 1hr

CURCUMINOIDS AND ITS METABOLITES FOR THE APPLICATION IN ALLERGIC OCULAR/NASAL CONDITIONS

RELATED APPLICATIONS

The present application is a Continuation of International Application Number PCT/IN2010/000166, entitled "Curcuminoids and Its Metabolites for the Application in Allergic Ocular/Nasal Conditions," filed on Mar. 22, 2010 and now published as WO 2010/109482. International Application Number PCT/IN2010/000166 is incorporated by reference in its entirety.

TECHNICAL FIELD

The present disclosure relates to a therapeutic aqueous nasal composition for nasal administration comprising an emulsion of natural or synthetic curcuminoids and/or their metabolites. The compositions are useful for the prevention or treatment of allergic nasal conditions and their associated symptoms in humans and animals.

BACKGROUND

The eye is a complex and sensitive organ of the body, which can experience numerous diseases. The eye poses many barriers to protect any damage to its tissues. This also means that the anterior portion of the eye is more susceptible to diseases. The first and foremost barrier is the conjunctiva, which is the mucous membrane surrounding the eye ball. It is constantly exposed to many harsh conditions/allergens through the environmental factors it encounters. This leads to the allergic reactions in the eye mediated by mast cells through the release of histamine leading to the condition called allergic conjunctivitis or other associated inflammatory conditions like redness and swelling of the eye. These allergic conditions are either seasonal which occurs only during specific time of the year and is termed seasonal allergic conjunctivitis (SAC) or perennial that occurs throughout the year and termed perennial allergic conjunctivitis (PAC). Some allergic conditions extend even to the cornea such as atopic keratoconjunctivitis, vernal conjunctivitis and giant papillary conjunctivitis.

These conditions are typically characterized by red, itchy and swollen eyes with watery discharge. This is largely attributed to the degranulation of mast cells due to the cross-linking of IgE upon allergen sensitization leading to an outburst of histamine in the conjunctiva. The conjunctiva being rich in mast cells, experiences an overdose of histamine upon allergen sensitization, resulting in the itching and redness of the eye. Current treatment methods involve anti-histamine drops (emedastine difumarate and levocabastine), topical mast cell stabilizers (olopatadine, ketotifen), decongestants and topical anti-inflammatory drugs (NSAID's and corticosteroids).

Allergic rhinitis is an inflammation of the nasal passages, usually associated with watery nasal discharge and itching of the nose and eyes. The symptoms occur in the nose and eyes and usually occur after exposure to dust, danders, or certain seasonal pollens. Patients can be severely restricted in their daily activities, resulting in excessive time away from school or work. Millions of dollars are spent each year on physician services and medication for treatment of this chronic illness. Many perennial and seasonal allergens cause allergic rhinitis the former giving rise to perennial allergic rhinitis (PAR) and the latter giving rise to seasonal allergic conjunctivitis (SAR).

Dust mites, cockroaches, molds and animal dander, are examples of year-around allergens.

Characteristic symptoms include repetitive sneezing; rhinorrhea (runny nose); post-nasal drip; nasal congestion; pruritic (itchy) eyes, ears, nose or throat; and generalized fatigue. Symptoms can also include wheezing, eye tearing, sore throat, and impaired smell. A chronic cough may be secondary to postnasal drip, but should not be mistaken for asthma. Sinus headaches and ear plugging are also common.

Anti-Histamines and Decongestants for Allergic Conjunctivitis

Anti-histamines are available for treating Allergic Conjunctivitis and are available in the market as tablets, capsules and liquids, and may or may not be combined with decongestants. Common anti-histamines include brompheniramine or chlorpheniramine, and clemastine. Non-sedating (less likely to cause drowsiness) long-acting anti-histamines include loratidine and fexofenadine. Oral decongestants alone may be helpful, including pseudoephedrine.

Nasal Sprays

For rhinorrhea, a nasal spray of cromolyn sodium (Nasalcrom) or a steroid nasal spray, such as flunisolide (Nasalide), beclomethasone dipropionate (Beconase, Vancenase), triamcinolone acetonide (Nasacort), and fluticasone (Flonase), may work so well that additional anti-histamines or decongestants are unnecessary. It is important to remember that improvement may not occur for one to two weeks after starting therapy with steroid nasal sprays. Short courses of oral corticosteroids may usually be indicated when severe nasal symptoms prevent the adequate delivery of topical agents. But due to their unpleasant side-effects, there has been a tremendous surge in demand for non-steroidal, plant based anti-inflammatory and anti-allergic agents and their potential use in various therapeutic applications. Curcuminoids are one such class of compounds that have proven anti-inflammatory and anti-allergic properties.

Curcuminoids are natural, polyphenolic compounds present in turmeric in three different forms a) Curcumin b) Bisdemethoxy curcumin and c) Demethoxy curcumin. Curcumin is the principal curcuminoid and has exceptionally potent antioxidant and anti-inflammatory activity, which can prevent cell damage caused by free-radicals (oxidative stress) and inflammation. The current level of interest on curcumin and its analogs/derivatives is known from the below mentioned articles.

Process for producing enriched fractions of bis-o-demethylcurcumin and tetrahydrotetrahydroxy-curcumin from the extracts of *curcuma longa* is disclosed in our earlier PCT Application #WO/2007/043058. According to this publication, bis-o-demethyl curcumin shows most potent anticancer, anti-oxidative and anti-inflammatory activity when compared to other curcuminoids and the natural mixture of curcumins.

However, the use of natural curcuminoids, such as curcumin, bisdemethoxycurcumin demethoxycurcumin and synthetically derived bis-o-demethyl curcumin and/or other demethylated curcuminoids either alone or in combination in ophthalmic formulations is not known in the prior art. Natural curcuminoids, such as curcumin, bisdemethoxycurcumin demethoxycurcumin and synthetically derived bis-o-demethyl curcumin and/or other demethylated curcuminoids either alone or in combination being a lipophilic drug have low aqueous solubility, and hence restrict the therapeutic availability of the same.

All curcuminoids, both natural and synthetic have lipophilic structures with conjugated double bonds with a keto group thus rendering them to have a dielectric constant which will interact with negatively charged membranes making it unable to permeate through the biological membrane. Thus, for these curcuminoids to pass through membranes, it is necessary to encapsulate these molecules with lipophilic molecules. Moreover, it is necessary to make the lattice of molecules as a single entity so that these encapsulated molecules can be transported across membranes.

Anti-allergic and anti-inflammatory drugs are classified into analgesics, anti-histamines, anti-microbials, corticosteroids and non steroidal anti-inflammatory drugs (NSAIDs). These classes of drugs are used to treat variety of ocular disorders. Prolonged use of corticosteroids, NSAIDs, and the other groups of above mentioned classes of drugs results in glaucoma, optic nerve damage, vision problems, cataract, or secondary ocular infections.

Accordingly, the current disclosure provides a potential successor in the field of ophthalmology with a novel phytopharmaceutical composition for the treatment of ocular and nasal diseases/disorders. Surprisingly, preliminary experiments conducted have demonstrated the use of surfactants and cosolvents in solubilizing curcuminoids up to 200 mg w/v thereby aiding effective solubilization in aqueous medium. The current method involves coating of curcuminoids using surfactants and a cosolvent in order to enhance the curcuminoids aqueous solubility and hence its permeation across the cell membrane.

Therefore, the current disclosure describes hitherto unexploited and novel ophthalmic composition(s) comprising natural curcuminoids, such as curcumin, bisdemethoxycurcumin demethoxycurcumin and synthetically derived bis-o-demethyl curcumin and/or other demethylated curcuminoids either alone or in combination, together with surfactants and/or cosolvents as aqueous ophthalmic composition(s) in the form of gel/suspension/ointment for ocular diseases or disorders.

SUMMARY

In a first aspect, the disclosure describes a formulation for nasal administration comprising a liquid medium and natural or synthetic curcuminoids and/or their metabolites. The curcuminoids or metabolites thereof may be curcumin, bis-demethoxycurcumin, demethoxycurcumin, or synthetically derived bis-O-demethyl curcumin and/or other demethylated curcuminoids. The curcuminoids may be present in the formulation alone or optionally in combination with a surfactant and/or a cosolvent, along with suitable ophthalmic excipients for inflammatory diseases of the eye such as allergic conjunctivitis. The curcuminoids may be nano-emulsified in the liquid medium, which serves as a carrier for the curcuminoids.

In another aspect, the disclosure describes a nasal spray comprising natural curcuminoids and/or its metabolites, such as curcumin, bisdemethoxycurcumin, demethoxycurcumin and/or synthetically derived bis-o-demethyl curcumin and/or other demethylated curcuminoids either alone or in combination with nonionic surfactant, cosolvent along with suitable excipients for inflammatory diseases of nose such as allergic rhinitis.

In another aspect, the disclosure describes formulation for nasal application enclosed herewith is a spray comprising curcumin, bisdemethoxycurcumin, demethoxycurcumin and/or synthetically derived bis-o-demethyl curcumin and/or other demethylated curcuminoids either alone or in combination with pharmaceutically acceptable excipients or suitable nasal excipients.

In another aspect, the disclosure describes compositions comprising one or more *Curcuma* derived components obtained naturally or by synthesis or semi-synthesis for preparing compositions described in the present disclosure.

In another aspect, the method of administration of natural curcuminoids and/or its metabolites, like curcumin, bisdemethoxycurcumin, demethoxycurcumin and/or synthetically derived bis-o-demethyl curcumin and other demethylated curcuminoids either alone or optionally in combination with a pharmaceutically acceptable excipients or carriers or diluents in a therapeutically effective amount to prevent, retard the development or to reduce the symptoms of several inflammatory diseases such as allergic conditions of the nasal tract.

In another aspect the disclosure describes use of the disclosed compositions for prevention and treatment of nasal allergic conditions in animals and humans.

In yet another aspect the disclosure describes methods for treating or preventing nasal allergic conditions in animals and humans, wherein said method comprises administration of therapeutically effective amount of the disclosed compositions.

DETAILED DESCRIPTION

Figure 1:
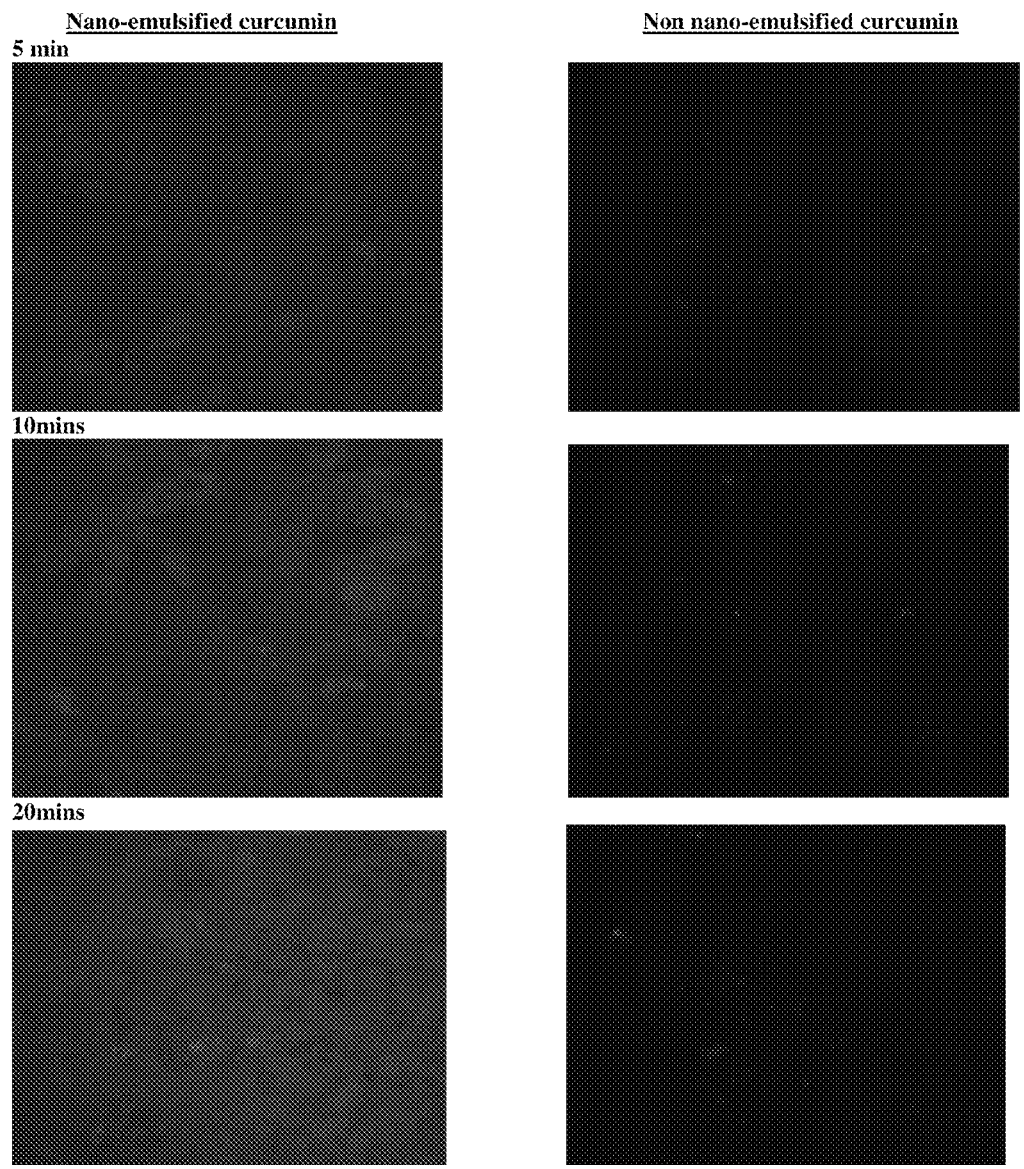
FIG. 1 depicts a comparison of intracellular transport of nanoemulsified curcumin with plain curcumin and the confocal pictures of nano emulsified curcuminoids and non-nano emulsified curcuminoids at 5 minutes, 10 minutes and 25 minutes.

Various embodiments are now described, so that various aspects thereof may be more fully understood and appreciated.

As used herein the term 'curcuminoid' or 'curcuminoids' means one or more *curcuma* derived components comprising natural curcuminoids, such as curcumin, bisdemethoxycurcumin, demethoxycurcumin and/or synthetically derived bis-o-demethyl curcumin and/or other demethylated curcuminoids either alone or optionally in combination with one or more pharmaceutically acceptable excipients for several inflammatory and allergic diseases in humans and animals in need thereof.

As used herein the term 'surfactant' or 'surfactants' means surface active agent(s) which works by lowering the surface tension of water and enabling solubility of lipophilic compounds.

The surfactants in nature are amphiphilic, meaning they contain a hydrophobic tail and a hydrophilic head. Therefore, these are soluble in both hydrophobic medium and water. The surfactants are of 2 types a) ionic (anionic and cationic) b) nonionic. The current disclosure describes the use of anionic, cationic and/or nonionic surfactants for pharmaceutical purposes. The surfactants used in the current disclosure can be selected from but not limited to polysorbate 80 and 20, poloxamers, octoxynol and any other pharmaceutically acceptable surfactant(s) suitable for preparing the compositions of the present disclosure.

Accordingly, in one embodiment, the current disclosure provides an aqueous ophthalmic (topical) eye drop or ophthalmic gel formulation comprising one or more *Curcuma* derived component(s) and their metabolites preferably selected from natural curcuminoids, such as curcumin, bisdemethoxycurcumin, demethoxycurcumin and/or synthetically derived bis-o-demethyl curcumin and/or other demethylated curcuminoids either alone or optionally in combination with pharmaceutically acceptable surfactant(s), cosolvent or suitable ophthalmic excipient(s).

In another embodiment, the disclosure provides a nasal spray comprising one or more *Curcuma* derived component(s) and their metabolites preferably selected from natural curcuminoids, such as curcumin, bisdemethoxycurcumin, demethoxycurcumin and/or synthetically derived bis-o-demethyl curcumin and/or other demethylated curcuminoids either alone or in combination along with suitable excipient(s).

In yet another embodiment, the present disclosure provides an aqueous ophthalmic (topical) eye drop or ophthalmic gel formulation comprising an effective amount of natural/synthetic curcuminoids and an amount of pharmaceutically acceptable surfactant(s) and a cosolvent or suitable ophthalmic excipient(s) effective in increasing the bioavailability of the lipophilic curcuminoids, when administered topically to the eye or an ointment comprising an effective amount of natural/synthetic curcuminoids administered topically to the eye to effectively treat several inflammatory and allergic conditions of the eye and nasal tract.

The present disclosure also provides an ophthalmic eye drop dispenser containing an ophthalmic (topical) composition comprising an effective amount of natural/synthetic curcuminoids, and a pharmaceutically acceptable surfactant(s) and a cosolvent in a therapeutically effective amount to effectively increase the solubility of the naturally active or synthetic component(s) used for preparing the composition(s). The composition(s) of this disclosure are devoid of any side effects and also effective in prolonging the therapeutic effect of the active agent, when administered to the eye.

The present disclosure also provides a nasal spray container comprising a nasal spray composition of an effective amount of one or more natural/synthetic curcuminoids, and in combination with an amount of pharmaceutically acceptable agent(s) such as nonionic surfactant(s) and a cosolvent(s) or suitable nasal excipient(s) effectively to increase the solubility of the naturally active or synthetic component(s) used for preparing the composition(s).

The disclosure describes pharmaceutical drug(s) derived from one or more *Curcuma* component(s) obtained either naturally or by synthetic or by semi-synthesis. *Curcuma* or Turmeric is a commonly used spice and coloring agent used in India, and is available from wide sources, having potent antiinflammatory, anti-oxidant and anti-allergic action with no side effect.

Curcumin was reported to have anti-allergic properties with inhibitory effect on histamine release from mast cells. The effectiveness of curcumin in allergy and asthma has been further investigated using a murine model of allergy. The results indicate a marked inhibition of allergic response in animals treated with curcumin suggesting a major role for curcumin in reducing the allergic response. The present review focuses on the results of research aimed to understand the immunomodulation induced by curcumin and its associated roles in the amelioration of allergy. These findings needed further evaluation, extrapolation, and confirmation before using curcumin for controlling allergy and asthma in humans. Kurup et al., "*Immunomodulatory effects of curcumin in allergy*" *Mol Nutr Food Res.* 2008 September; 52(9):1031-9

The desirable preventive or putative therapeutic properties of curcumin have also been considered to be associated with its antioxidant and anti-inflammatory properties. Free radical-mediated peroxidation of membrane lipids and oxidative damage of DNA and proteins are believed to be associated with a variety of chronic pathological complications such as cancer, atherosclerosis, and neurodegenerative diseases. Curcumin is thought to play a vital role against these pathological conditions. The anti-inflammatory effect of curcumin is most likely mediated through its ability to inhibit cyclooxygenase-2 (COX-2), lipoxygenase (LOX), and inducible nitric oxide synthase (iNOS). COX-2, LOX, and iNOS are important enzymes that mediate inflammatory processes. Improper upregulation of COX-2 and/or iNOS has been associated with the pathophysiology of certain types of human cancer as well as inflammatory disorders. Because inflammation is closely linked to tumor promotion, curcumin with its potent anti-inflammatory property is anticipated to exert chemopreventive effects on carcinogenesis. Hence, the past few decades have witnessed intense research devoted to the antioxidant and anti-inflammatory properties of curcumin. In this review, both antioxidant and anti-inflammatory properties of curcumin, the mode of action of curcumin, and its therapeutic usage against different pathological conditions are clearly described. Menon V P et al., *Antioxidant and anti-inflammatory properties of curcumin Adv Exp Med Biol.* 2007; 595: 105-25

Anti-asthmatic property of curcumin (diferuloylmethane), a natural product from the rhizomes of *Curcuma longa*, has been tested in a guinea pig model of airway hyperresponsiveness. The guinea pigs were sensitized with ovalbumin (OVA) to develop certain characteristic features of asthma: allergen induced airway constriction and airway hyper reactivity to histamine. Guinea pigs were treated with curcumin during sensitization (to examine its preventive effect) or after developing impaired airways features (to examine its therapeutic effect). Status of airway constriction and airway hyper reactivity were determined by measuring specific airway conductance (SGaw) using a non-invasive technique, constant-volume body plethysmography. Curcumin (20 mg/kg body weight) treatment significantly inhibits OVA-induced airway constriction ($p<0.0399$) and airway hyper reactivity ($p<0.0043$). The results demonstrate that curcumin is effective in improving the impaired airways features in the OVA-sensitized guinea pigs. Arjun Ram et al., *Curcumin Attenuates Allergen-Induced Airway Hyperresponsiveness in Sensitized Guinea Pigs, Biological & Pharmaceutical Bulletin* Vol. 26 (2003), No. 7 1021

Thus keeping in mind the above cited references and many other references, in the present disclosure it was aimed to the study under trial and to test the benefits of the formulation of curcumin in the treatment or prevention of several inflammatory diseases of eye and nose such as Allergic Conjunctivitis/Allergic Rhinitis which is characterized primarily by itching, redness and edema of the eye due to histamine release.

Accordingly, the present disclosure provides ophthalmic compositions/formulation in any suitable form, more specifically as ophthalmic drops or ophthalmic gel, where the formulation may comprise one or more *Curcuma* derived components such as curcuminoids available from natural or obtained by synthesis or semi-synthesis.

In a preferred embodiment, the active agents that may be used include, but are not limited to, constituents of natural curcumin mixture comprising natural curcuminoids, such as curcumin, bisdemethoxycurcumin, demethoxycurcumin and/or synthetically derived bis-o-demethyl curcumin and/or other demethylated curcuminoids either alone or in combination having antioxidant or anti-inflammatory activity. The concentration of total curcuminoids in the compositions of the present disclosure may vary from 0.01% to 5.0% w/v and more preferably between 0.05% to 2.5%, with an effective concentration of 0.06%. The curcumin components can be derived from one or more *curcuma* species comprising *Curcuma longa, Curcuma aromatica* and *Curcuma Zedoaria*.

According to the disclosure the drug and surfactants can be combined with acceptable carriers to formulate a stable ophthalmic preparation with enhanced bioavailability and stability. These carriers include pharmaceutically acceptable excipients and additives selected from but not limited to water soluble polymers, chelating agents, stabilizing agents, isotonizing agents, buffer substances, preservatives, thickeners, complexing agents, electrolytes and other excipients.

The water soluble polymers are selected from but not limited to methylcellulose, hydroxyethyl cellulose, hydroxypropyl cellulose, hydroxypropyl methylcellulose, hydroxypropyl ethylcellulose, sodium carboxymethylcellulose, polyvinyl alcohol, polyvinylpyrrolidone, polyethylene glycol, poly(methyl methacrylate), polycarbophil, gelatin, alginate, poly(acrylic acid), polyethylene oxide and chitosan or a derivative thereof.

The surfactant(s) can be anionic, cationic or non-ionic, selected from but not limited to polysorbate 80 and 20, polyethylene glycol esters, polyethylene glycols, glycerol ethers or mixtures of those compounds.

The co-solvents are selected from but not limited to monohydric alcohol or polyhydric alcohols such as polyethylene glycol, polypropyleneglycol and the like.

The composition further comprises a chelating agent such as disodium salt of EDTA. The composition may comprise suitable water soluble polymers which may be used in the disclosed compositions, including, but not limited to methylcellulose, hydroxyethyl cellulose, hydroxypropyl cellulose, hydroxypropyl methylcellulose, hydroxypropyl ethylcellulose, sodium carboxymethylcellulose, polyvinyl alcohol, polyvinylpyrrolidone, polyethylene glycol, poly(methyl methacrylate), polycarbophil, gelatin, alginate, poly(acrylic acid), polyethylene oxide and chitosan or a derivative thereof.

The stabilizing agent in the present composition comprises of but is not limited to sodium hydrogen sulfite, glycerin, sodium citrate, butyl hydroxyanisole, benzalkonium chloride, edetic acid and pharmaceutically acceptable salts thereof, tocopherol and derivatives thereof, optionally in combination with sodium edetate.

The isotonizing agent used in the composition comprises of but is not limited to any specific one like sodium chloride, potassium chloride, D-mannitol, glucose, glycerin, xylitol and propylene.

In various embodiments, the thickening agent is methylcellulose, ethyl cellulose, hydroxypropyl methylcellulose, polyvinyl pyrrolidone, polyvinyl alcohol, sodium chondroitin sulfate, sodium hyaluronate or chitosan; however, the thickening agent is not limited to these polymers. Thickening agents are used to maintain the viscosity of the liquid formulations. Accordingly, the pharmaceutical composition(s) for nasal administration of the present disclosure comprise one or more nanoemulsified curcumin component or a metabolite thereof, selected from natural or synthetic curcuminoid(s). The compositions have a viscosity in the range of 5-20 centipoises.

The preservatives which may be used include but not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol.

The buffering agents that may be used include, but are not limited to, sodium carbonate, sodium tetraborate, sodium phosphate, sodium acetate, sodium bicarbonate.

Electrolytes such as sodium chloride and potassium chloride may also be included in the formulation.

The ophthalmic/intra-nasal aqueous pharmaceutical preparation of the present disclosure may be charged in an appropriate container for better drug delivery.

The dosage form of the ophthalmic aqueous pharmaceutical preparation of the present disclosure is not limited to an eye drop, but may be prepared as ophthalmic gel. For instance, the ophthalmic aqueous pharmaceutical suspension preparation of the present disclosure can widely be used for the treatment of all the anterior and posterior related conditions or ocular diseases.

The dosage form of the intra-nasal aqueous pharmaceutical preparation of the present disclosure is not limited to nasal spray and can be prepared as nasal drops also.

Furthermore, the ophthalmic/nasal aqueous solution preparation of the present disclosure comprises a non-steroidal drug. Therefore, it may be devoid of any side effect even if it is administered for a prolonged period of time with a low probability of damaging corneal/nasal epithelial cells or the conjunctival cells.

Potent curcuminoids such as curcumin, bis-o-demethyl curcumin suppress inflammation by inhibiting edema, fibrin deposition, capillary leakage and phagocytic migration, all key features of the inflammatory response. These curcuminoids prevent the release of prostaglandins, some of which have been identified as mediators of cystoid macular edema. Additionally, curcuminoids including bis-o-demethyl curcumin have been shown to inhibit the expression of vascular endothelial growth factor (VEGF), a cytokine which is a potent promoter of vascular permeability.

In order to further validate the hypothesis of the anti-allergic activity of curcuminoids certain ex-vivo and in vivo studies can be performed. Guinea pig ileum study would be an ideal ex-vivo experiment where the allergen sensitized guinea pig ileum is treated with the formulation and assessed for its efficacy. In the same way the formulation can be tested in vivo by sensitizing the animals with histamine and treating with the formulation and assessing for its efficacy.

The use of curcuminoids to date, by conventional routes of administration, has yielded limited success in treating eye disorders, including macular edema, largely due to the inability to deliver and maintain adequate quantities of the drug to the posterior segment without resultant toxicity. For example, after usual topical administration of ophthalmic drops, only about 1% reaches the anterior segment, and only a fraction of that amount moves into the posterior segment. Although intravitreal injections of drug have been used, the exposure to the drug is very brief as the half-life of the drug within the eye is approximately 3 hours.

In our previous Indian patent application#PCT/IN2009/000651, a process of solubilization of natural or synthetic curcumin and other curcuminoids has been described using surfactants and cosolvents with the help of sonar energy.

It was also found that the nanoemulsified curcumin was effectively taken up by the cells when compared to the normal curcumin. The nanoemulsified curcumin increases the pharmacokinetics and pharmacodynamics properties thereby having a better therapeutic effect. This process enhances the uptake of curcumin and thereby having a potent therapeutic effect. The nanoemulsification process enhances the anti-allergic activity of curcumin thus increasing the effectiveness of the formulation when compared with any other known therapeutic agents.

The nanoparticle size of curcumin in the present disclosure was found to be between 10-20 nm in size. However, the nanodroplet size can vary from 5-500 nm, preferably 5-100 nm and more preferably 5-30 nm. Transmission electron microscope (TEM) and Scanning electron microscope (SEM) studies were conducted on the nanoemulsion to confirm the shape and size of the nano particles.

A typical eye drop/nasal spray formulation(s) of the present disclosure comprises of one or more Curcumin derived components selected from an aqueous drug suspension of solid natural curcuminoids, such as curcumin, bis-demethoxycurcumin demethoxycurcumin and synthetically derived bis-o-demethyl curcumin and/or other demethylated curcuminoids with antioxidant or anti-inflammatory activity optionally in combination with pharmaceutically acceptable excipient(s) selected from but not limited to nonionic surfactant preferably cyclodextrin complexes, water-soluble polymers such as hydroxypropyl methylcellulose, and other cellulose derivatives, chelating agent, metal ions (such as magnesium ions) and/or organic salts such as sodium acetate and sodium citrate, where such additives are used to stabilize the system with enhanced mucoadhesive properties.

In yet another embodiment, the disclosure describes use of the disclosed compositions for prevention and treatment of ocular and nasal allergic conditions in animals and humans.

Use of the compositions disclosed herein is applicable for prevention and treatment of conditions associated with eye such as allergic conjunctivitis, atopic keratoconjunctivitis, vernal conjunctivitis, giant papillary conjunctivitis and conditions thereof.

Use of the compositions disclosed herein is applicable for treatment and prevention of conditions associated with nose such as allergic rhinitis. The disclosure further provides the use of the recited compositions is applicable for treatment and prevention of asthma.

In another embodiment, the method of administration of natural curcuminoids and/or its metabolites, like curcumin, bisdemethoxycurcumin, demethoxycurcumin and/or synthetically derived bis-o-demethyl curcumin and other demethylated curcuminoids either alone or optionally in combination with a pharmaceutically acceptable excipients or carriers or diluents in a therapeutically effective amount to prevent, retard the development or to reduce the symptoms of several inflammatory diseases such as allergic conditions of the eye/conjunctiva and/or the nasal tract.

In another embodiment, the disclosure describes methods of reducing or preventing or retarding the development of conditions associated with the eye such as allergic conjunctivitis, atopic keratoconjunctivitis, vernal conjunctivitis, giant papillary conjunctivitis which comprise administering an effective amount of the disclosed compositions to a subject suffering with said conditions.

In another embodiment, the disclosure describes a method of treating and preventing Asthma comprises administering an effective amount of the disclosed composition to a subject suffering with asthma.

In yet another embodiment, the disclosure describes a method of treating and preventing conditions associated with the nose such as allergic rhinitis, which comprises administering an effective amount of the disclosed composition to a subject suffering with said conditions.

The subject mentioned in the above methods is animal or humans.

Having described various embodiments, other embodiments will become apparent to one skilled in the art from consideration of the specification. The invention is further described by reference to the following non-limiting examples. It will be apparent to those skilled in the art that any modifications, both to materials and methods, may be practiced without departing from the scope of the invention.

EXAMPLES

Example 1

Preparation of Formulation-1

TABLE 1

| S. No | Ingredients | Concentration |
|---|---|---|
| 1 | Natural/synthetic curcuminoid | 20-2500 mg |
| 2 | Polyethylene Glycol | 0.7 g-1 g |
| 4 | Tween 80 | 0.7 g-1 g |
| 6 | Hydroxy Propyl Methyl Cellulose | 0.1 g |
| 7 | Benzalkonium Chloride | 20 mg |
| 8 | Ethylene Diamine Tetra Acetic Acid (disodium salt) | 100 mg |
| 9 | Sodium tetraborate (0.1M) | 3.81 g |
| 10 | Boric acid (1M) | 6.8 g |
| 11 | NaCl | 0.795 g |
| 12 | Sterile water for Injection | 100 ml |

Example 2

Preparation of Formulation-2

TABLE 2

| S. No | Ingredients | Concentration |
|---|---|---|
| 1 | Natural/synthetic Curcuminoid | 20-2500 mg |
| 2 | Polyethylene Glycol | 0.7 g-1 g |
| 4 | Tween 20 | 0.7 g-1 g |
| 6 | Hydroxy Propyl Methyl Cellulose | 0.1 g |
| 7 | Benzalkonium Chloride | 20 mg |
| 8 | Ethylene Diamine Tetra Acetic Acid (disodium salt) | 100 mg |
| 9 | Sodium tetraborate (0.1M) | 3.81 g |

TABLE 2-continued

| S. No | Ingredients | Concentration |
|---|---|---|
| 10 | Boric acid (1M) | 6.8 g |
| 11 | NaCl | 0.795 g |
| 12 | Sterile water for Injection | 100 ml |

Example 3

Preparation of Formulation-3

TABLE 3

| S. No | Ingredients | Concentration |
|---|---|---|
| 1 | Natural/synthetic Curcuminoid | 20-2500 mg |
| 2 | Polyethylene Glycol | 0.7 g-1 g |
| 4 | Octoxynol | 0.7 g-1 g |
| 6 | Hydroxy Propyl Methyl Cellulose | 0.1 g |
| 7 | Benzalkonium Chloride | 20 mg |
| 8 | Ethylene Diamine Tetra Acetic Acid (disodium salt) | 100 mg |
| 9 | Sodium tetraborate (0.1M) | 3.81 g |
| 10 | Boric acid (1M) | 6.8 g |
| 11 | NaCl | 0.795 g |
| 12 | Sterile water for Injection | 100 ml |

Example 4

Preparation of Formulation-4

TABLE 4

| S. No | Ingredients | Concentration |
|---|---|---|
| 1 | Natural/synthetic Curcumin | 20-2500 mg |
| 2 | Polyethylene Glycol | 0.7 g-1 g |
| 4 | Poloxamers | 0.7 g-1 g |
| 6 | Hydroxy Propyl Methyl Cellulose | 0.1 g |
| 7 | Benzalkonium Chloride | 20 mg |
| 8 | Ethylene Diamine Tetra Acetic Acid (disodium salt) | 100 mg |
| 9 | Sodium tetraborate (0.1M) | 3.81 g |
| 10 | Boric acid (1M) | 6.8 g |
| 11 | NaCl | 0.795 g |
| 12 | Sterile water for Injection | 100 ml |

Example 5

A Typical Nasal Formulation of 0.06% Curcumin

TABLE 5

| S. No | Ingredients | Concentration |
|---|---|---|
| 1 | Curcumin | 60 mg |
| 2 | Polyethylene Glycol | 1 g |
| 4 | Tween 80 | 1 g |
| 6 | Hydroxy Propyl Methyl Cellulose | 0.1 g |
| 7 | Benzalkonium Chloride | 20 mg |

TABLE 5-continued

| S. No | Ingredients | Concentration |
|---|---|---|
| 8 | Ethylene Diamine Tetra Acetic Acid (disodium salt) | 100 mg |
| 9 | Sodium tetraborate (0.1M) | 3.81 g |
| 10 | Boric acid (1M) | 6.8 g |
| 11 | NaCl | 0.795 g |
| 12 | Sterile water for Injection | 100 ml |

Example 6

Comparison of Intracellular Transport of Nanoemulsified Curcumin with Plain Curcumin Subject: Caco-2 cell incubated with 60 μg/ml concentration of nanoemulsified and plain curcumin were used in the study.

Experimental method: The study was conducted to evaluate the uptake of nanoemulsified curcumin intracellularly. Cells were grown on the transwell inserts to 100% confluence. The cells were then incubated with nanoemulsified and plain curcumin with a concentration of 60 μg/ml for 5 minutes, 10 minutes and 20 minutes. At a later stage the inserts were washed with HBSS buffer and fixed with 3% paraformaldehyde. The insert was then cut and mounted on a slide and covered with a cover slip. These slides were then studied under confocal microscope at 63×. The methodology of the test is detailed in Table-6 and the results are summarized in FIG. 1.

TABLE 6

| Cells | Caco-2 |
|---|---|
| Conc. Of Curcumin | 60 μg/ml |
| Treatment groups | 2(NE—nanoemulsified; NNE—non nanoemulsified |
| Incubation period | 5 min., 10 min. and 20 min. |

Example 7

Figure 2:
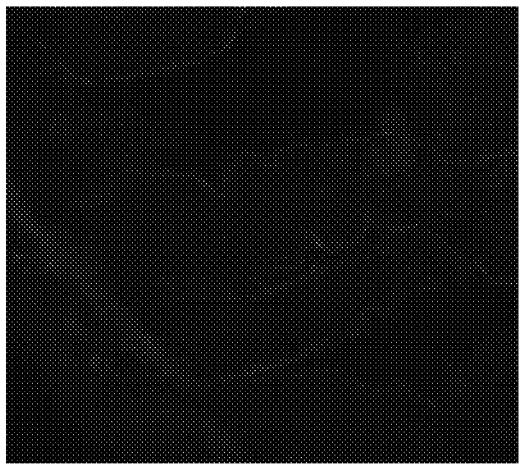
FIG. 2 depicts a comparison of intestinal uptake of nanoemulsified curcumin with plain curcumin and the confocal pictures of nano emulsified curcumin and non-nano emulsified curcumin at 1 hour time intervals in two different animal groups.
Figure 2:
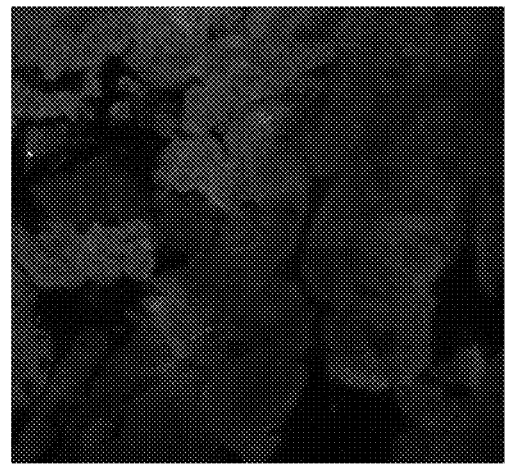
Figure 2:
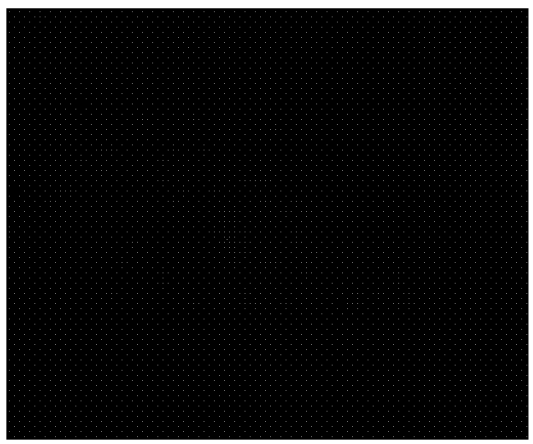
Figure 2:
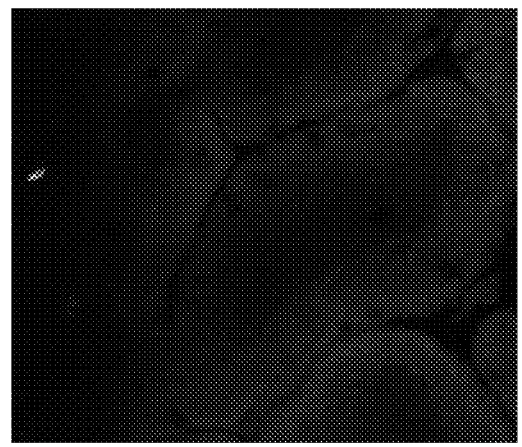

Comparison of the Uptake of Nanoemulsifed Curcumin Vs. Plain Curcumin into Intestinal Cells of Mice Using the Isolated Intestinal Loop Model Confocal microscopy studies were performed on cryosectioned mice intestinal tissue samples to determine the intracellular uptake of curcumin by the intestinal epithelial cells using the isolated intestinal loop model. Briefly the mice were anesthetized with xylazine/ketamine and cut open. Following this, the intestines were exposed and the ileum was identified and a loop was tied at the top and bottom of the ileum using surgical sutures without detaching from the mesenchymal system after flushing out the intestinal contents. The drug solutions at a concentration of 300 ug/ml for the respective groups were introduced into the lumen using a syringe with a polyethylene tube attached to the needle and incubated for 60 minutes. After 60 minutes the tissues were excised and frozen in liquid nitrogen immediately. The tissues were then subjected to cryosectioning and mounted on a slide and covered using a cover slip after which they were studied under the confocal microscope at 63×. The results are summarized in FIG. 2.

No. of groups:—2 (Nanoemulsified (NE); Plain Curcumin (NNE))
No. of animals/group:—2

Example 8

Particle Size Study Using Malvern Particle Size Analyzer

Figure 3:
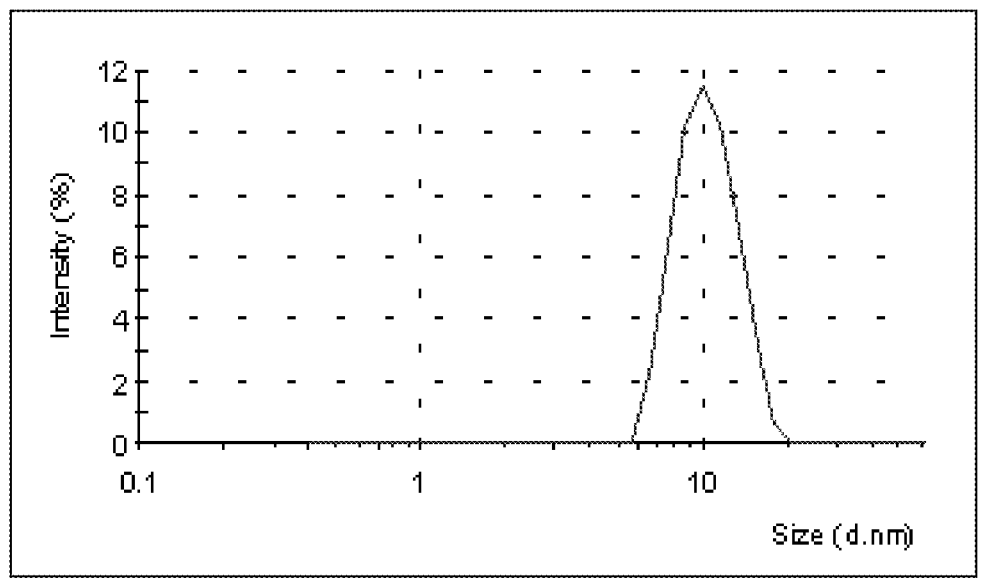
FIG. 3 depicts a Particle Size Study using a Malvern particle size analyzer.

The particle size is analyzed by using Malvern particle size analyzer. The particle size (powder, suspensions and emulsions) is measured by diffraction and diffusion of laser beam. For the purpose of laser diffraction measurement, the particles are exposed to a laser beam. The particles scatter light at an angle that is inversely proportional to their size. Photosensitive detectors are used to measure the angular intensity. A map of angle versus scattering intensity gives the particle size value. The droplet size of the nanoemulsions was determined by Malvern particle size analyzer particle analyzer and was found to be 10.55 nm. The results of particle size analysis by Malvern particle size analyzer are summarized in FIG. 3.

TABLE 7

| Peaks | Size of the particles | PDI |
| --- | --- | --- |
| Peak-1 | 10.55 | 0.2387 |

Example 9

Characterization of Nanoemulsion by TEM

Figure 4:
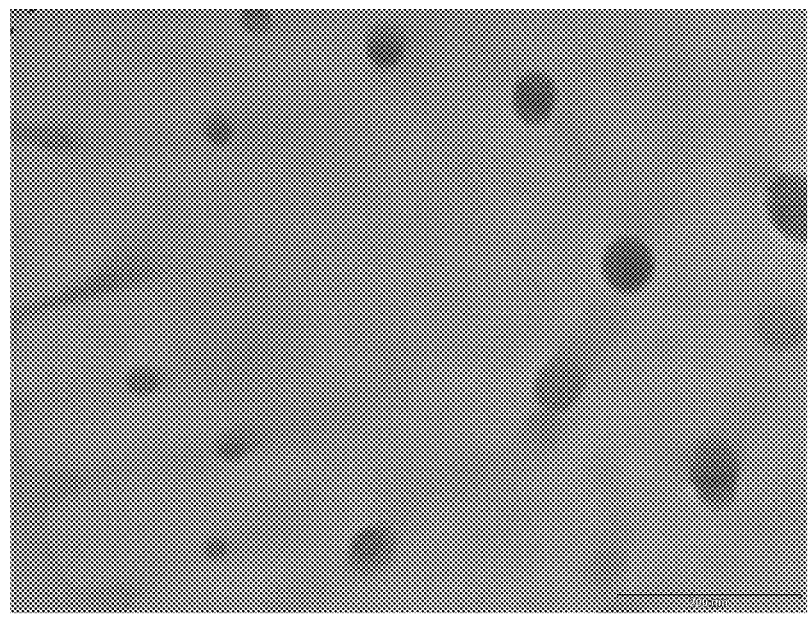
FIG. 4 depicts a TEM Micrograph: "Morphology of nano-emulsion under TEM."

The morphology and structure of the nanoemulsion were studied using transmission electron microscopy (TEM). A combination of bright-field imaging at increasing magnification and of diffraction modes was used to reveal the form and size of the nanoemulsion. To perform the TEM observations, the nanoemulsion formulation was diluted with water (1/100). A drop of the diluted nanoemulsion was directly deposited on the holey film grid and observed after drying. The image result of nanoemulsion clearly showed that the nanoparticles are spherical in shape and size varied from 10-20 nm. The TEM image of the nanoemulsion is shown in FIG. 4

Example 10

Characterization of Nanoemulsion by SEM

Figure 5:
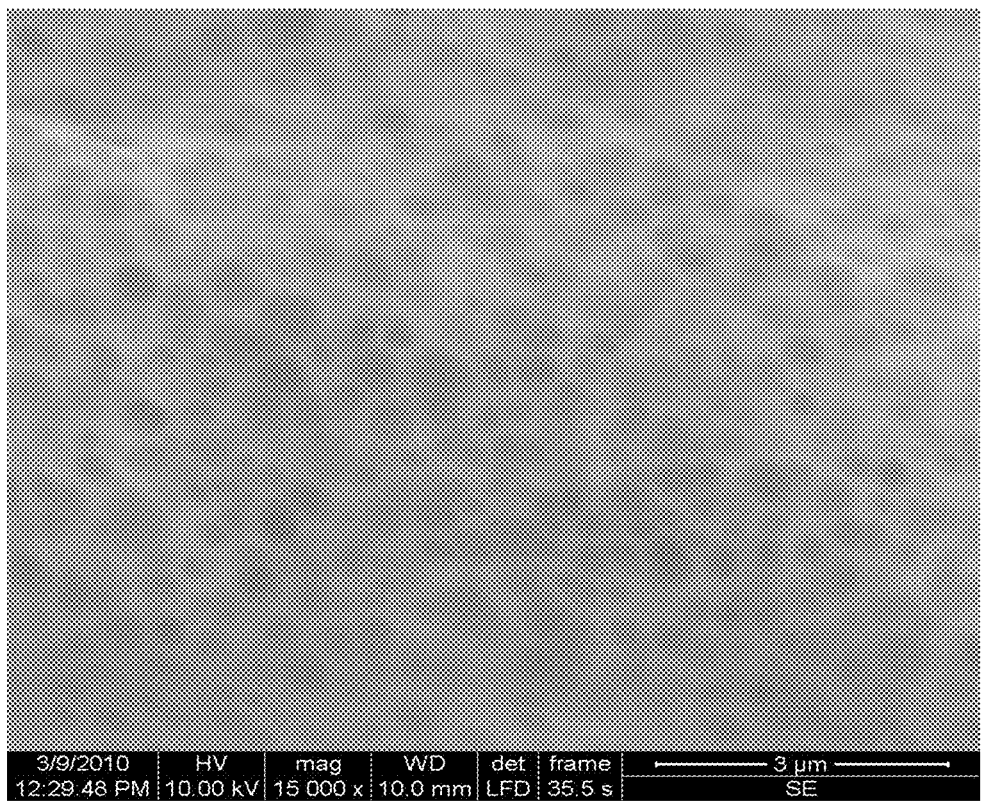
FIG. 5 depicts a SEM Micrograph: "Morphology of nano-emulsion under SEM."

SEM studies on the nanoemulsion showed that the particles were spherical in shape and size was in nanometer range (FIG. 5). The particle size was in the range of 10-20 nm.

Example 11

FRAP Assay (Total Antioxidant Activity) for Curcumin

The FRAP assay (TPTZ assay) developed by Benzie and Strain [R] was employed to measure the total antioxidant activity of the Curcumin in comparison to Vitamin C and Gallic acid. The assay mixture contained 2.5 mL 300 mM acetate buffer pH 3.6, 0.25 mL 10 mM TPTZ solution in 40 mM HCl, 0.25 mL 20 mM FeCl3 and Curcumin in 0.1 mL water or methanol. 30 minutes after incubation the absorbance was measured at 593 nm using Cary-50, UV-Vis spectrophotometer. Standard graphs were constructed using known concentrations of ferrous salt in water/methanol to replace $FeCl_3$. All tests were run in triplicate and mean values were used to calculate EC1 values. EC1 is defined as concentration of antioxidant having a ferric reducing ability equivalent to that of 1 mM ferrous salt.

Figure 6:
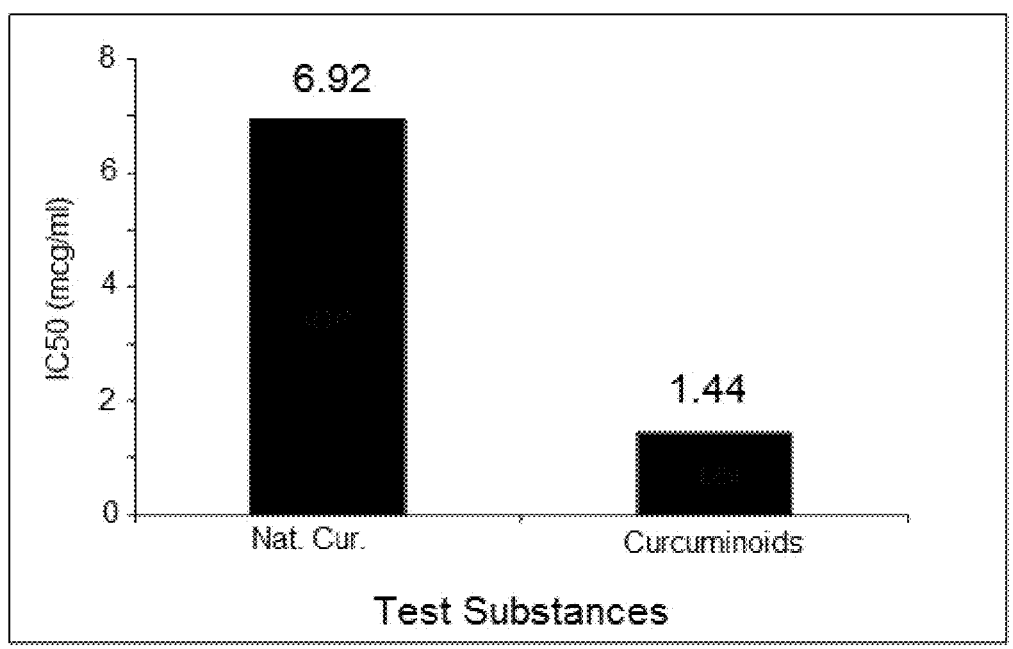
FIG. 6 depicts a FRAP assay showing total anti-oxidant activity of curcumin

Result: The $IC_{50}$ value in mcg/ml was found to be 6.92 for natural curcumin (FIG. 6).

Example 12

Anti-Allergic Study

The pre-clinical model used for the ocular allergy study is based on sensitizing the animals against the allergen egg albumin followed by challenging the conjunctiva by egg albumin to produce ocular allergy. Twenty four animals (SD rats) in the age group of 10 to 14 weeks were used for this study, comprising of four groups with 6 animals in each group. Group 1 serves as a naïve control (neither induced nor treated), group 2 serves as the egg albumin induced group, group 3 serves as the curcumin ophthalmic drops treated group and group 4 animals are treated only with the vehicle used for ophthalmic solution preparation. All the animals in the group 2, group 3 and group 4 are sensitized with 1 ml intraperitoneal injection of suspension containing 100 µg egg albumin and 20 mg alum for 14 days. On $15^{th}$ day 10 µl of 1M DL-Dithiothreitol (DTT) in Phosphate buffered saline (pH—7.4) was applied to the conjunctiva and 10 mM later the conjunctiva was topically challenged with 10 µl egg albumin (100 mg/ml) prepared in phosphate-buffered saline to produce ocular allergy. Drug efficacy was tested by installing the Curcumin based ophthalmic solution to the eye of rats in group 3 by gently opening the eyelids of the rats 10 minutes before the DTT and allergen challenge. The animals in group 4 were treated with the similar manner with the vehicle. The hyperemia and edema of the conjunctiva was then measured on a 0-4 point conjunctival scoring system at 0 mM, 20 mM, 45 mM, 90 mM and at the end of $4^{th}$ hour and the effectiveness of the drug was shown by the reduction in conjunctival redness and conjunctival edema when compared to baseline.

Example 13

Inhibition of β-Hexosaminidase by Nanoemulsified Curcumin

In a present study, the comparative efficacies on inhibition of β-Hexosaminidase release by unformulated and formulated compositions of curcumin (nanoemulsified) in Phorbol ester (PMA) induced model of U937 human monocyte was assessed. Briefly, an equal number (50,000 cells) of U937 human monocytes was plated in each well of a 96-well cell culture plate. The cells were treated with different concentrations of unformulated and formulated compositions of curcumin in presence or absence of either 20 nM PMA. The cell culture supernatants collected from either untreated control or treated cultures were clarified at 10,000 g for 5 mM at 4° C.; and assessed for released β-hexosaminidase (6).

Measurement of Hexosaminidase

Twenty microliter aliquots of cell culture supernatant were incubated with 20 µl of 1 mM p-nitrophenyl-N-acetyl-β-D-glucosaminide in 0.1 M sodium citrate buffer (pH 4.5) at 37° C. for 1 h. At the end of the incubation, 250 p. 1 of a 0.1 M $Na_2CO_3$, 0.1 M $NaHCO_3$ buffer (pH 10.0) were added. Absorbance was measured at 405 nm. Each treatment was done in quadruplicate wells. The mean OD obtained from the control cultures was considered as 100% release of hexosaminidase.

Figure 7:
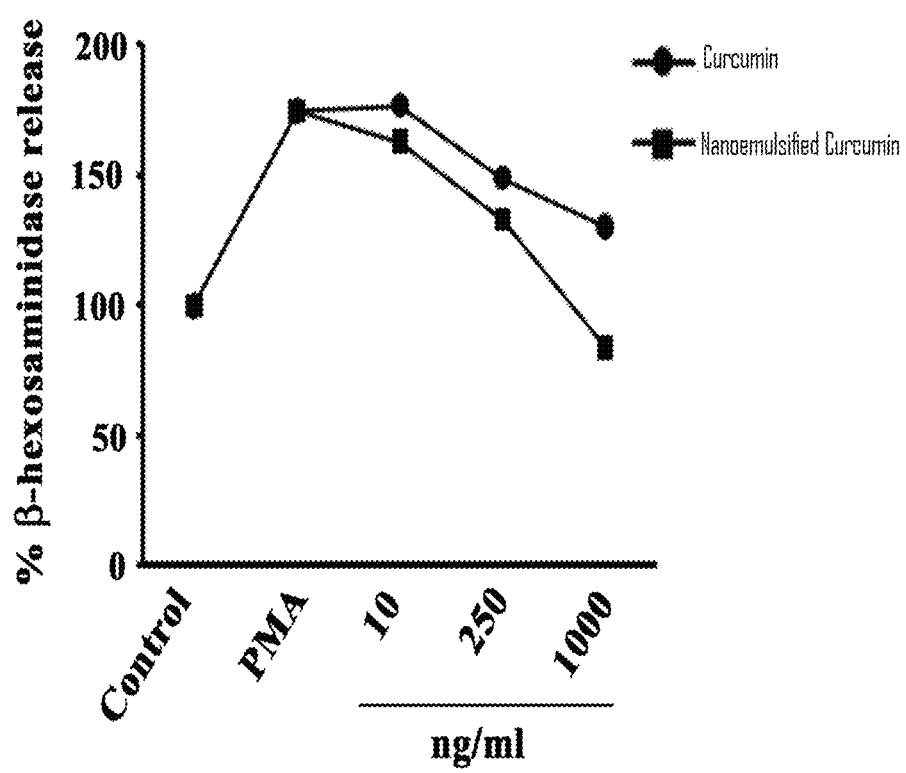
FIG. 7 depicts a line diagram showing inhibition of β-hexosaminidase release from PMA-induced U937 human monocytes concomitantly treated with different concentrations curcumin (formulated and non-formulated) as indicated. β-hexosaminidase released form the untreated control cells are considered as 100%. Results represented as the mean from quadruplicate culture wells.

The comparative efficacies in inhibiting β-hexosaminidase release by curcumin and its respective nanoemulsified formulations in PMA induced human monocytes are depicted in FIG. 7.

Example 15

Inhibition of Histamine Release by Nanoemulsified Curcumin

Figure 8:
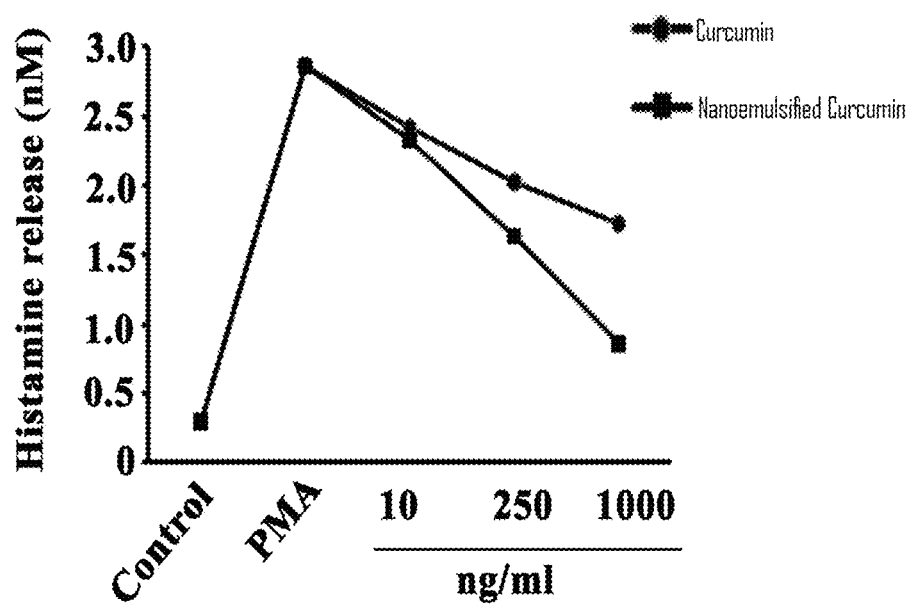
FIG. 8 depicts line diagram showing inhibition of histamine release from PMA-induced U937 human monocytes concomitantly treated with different concentrations of non-formulated and formulated curcumin.

An equal number (50,000 cells) of U937 human monocytes were plated in each well of 96-well cell culture plate. The cells were treated with different concentrations of non-formulated and formulated curcumin (nanoemulsified) compositions in presence or absence of 20 nM PMA for 1 h. The cell culture supernatants collected from either untreated control or treated cultures were clarified at 10,000 g for 5 mM at 4° C.; and assessed for released histamine by a commercially available EIA kit (SPI-Bio, France). The concentrations of the released histamine in the culture supernatants from PMA induced human monocytes treated with curcumin and its nanoemulsified formulations are depicted in FIG. 8.

Method for Preparation of the Formulation:
Preparation of Borate Buffer:
  1) 3.81 g of sodium tetraborate was weighed into a beaker and dissolved in 100 ml of water.
  2) 6.8 g of boric acid was weighed into a beaker and dissolved in 100 ml of water.
  3) pH of sodium tetraborate solution was checked and found to be in the range of 9. This was adjusted to a pH of 7.2 by the addition of boric acid.
  4) The buffer thus prepared was used to adjust pH of the formulation.
Solubilization of Curcumin:
  1) 60 mg curcumin was weighed into a 10 ml beaker
  2) To this 1 g (765 ul) Tween80® and 1 g PEG was added and stirred well using a glass rod.
  3) Following this the tube was sonicated for 30 min or until the curcumin was completely solubulized.
  A deep red color solution was formed.
Preparation of Ophthalmic Formulation:
  1) 100 ml water was placed into a beaker on a magnetic stirrer.
  2) HPMC was added and stirred till all the HPMC dissolved.
  3) The curcumin+Tween80® solution was added drop by drop into this and stirred for 15 mins
  4) To this BAC, EDTA and NaCl was added and stirred until all the contents dissolve completely and a yellow color clear solution was obtained.
  5) pH of the solution was checked and found to be in the range of 5.3-5.4. It was adjusted with the borate buffer to a pH of 6.5.

It will be evident to those skilled in the art that the invention is not limited to the details of the foregoing disclosure and its illustrative examples, and that the present invention may be embodied in other specific forms without departing from the essential attributes thereof. It is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A method of treating a nasal allergic condition, comprising nasally administering a pharmaceutical composition to an animal or a human exhibiting symptoms of a nasal allergy, wherein said pharmaceutical composition comprises:
    a nanoemulsified curcumin component, said curcumin component having a mean particle size of between 5 nm and 30 nm, wherein said curcumin component is selected from the group consisting of a natural curcuminoid, a synthetic curcuminoid, a metabolite of a natural or synthetic curcuminoid, and a mixture thereof;
    a liquid medium, wherein said liquid medium is an aqueous carrier, and
    a pharmaceutically acceptable excipient,
    said pharmaceutical composition being administered as a nasal spray or nasal drops.

2. The method according to claim 1, wherein the curcumin component comprises a compound selected from the group consisting of curcumin, bisdemethoxycurcumin, demethoxycurcumin, a demethylated curcuminoid, and a mixture thereof.

3. The method according to claim 1, wherein the synthetic curcuminoid is bis-O-demethyl curcumin.

4. The method according to claim 1, wherein the nanoemulsified curcumin component has a particle size between about 10 nm and about 20 nm.

5. The method according to claim 1, wherein the pharmaceutical composition comprises the nano emulsified curcumin component in an amount ranging from about 0.01% to about 5% w/v.

6. The method according to claim 5, wherein the pharmaceutical composition comprises the nano emulsified curcumin component in an amount ranging from about 0.05% to about 0.15% w/v.

7. The method according to claim 1, wherein the curcumin component comprises at least one compound derived from a species selected from the group consisting of *Curcuma longa, Curcuma aromatic, Curcuma zedoaria*, and combinations thereof.

8. The method according to claim 1, wherein the pharmaceutically acceptable excipient is selected from the group consisting of a surfactant, a co-solvent, and a mixture thereof.

9. The method according to claim 8, wherein the surfactant is selected from the group consisting of anionic surfactants, cationic surfactants, non-ionic surfactants, and mixtures thereof.

10. The method according to claim 8, wherein the surfactant is selected from the group consisting of polysorbate 80, polysorbate 20, polyethylene glycol esters, polyethylene glycols, glycerol ethers, and mixtures thereof.

11. The method according to claim 8, wherein the co-solvent is selected from the group consisting of monohydric alcohols, polyhydric alcohols, polyethylene glycols, polypropelene glycols, and mixtures thereof.

12. The method according to claim 1, wherein the composition further comprises at least one additive selected from the group consisting of a water soluble polymer, a chelating agent, a stabilizing agent, an isotonizing agent, a buffer substance, a preservative, a thickener, an electrolyte and mixtures thereof.

13. The method according to claim 12, wherein the water soluble polymer is selected from the group consisting of methylcellulose, hydroxyethyl cellulose, hydroxypropyl cellulose, hydroxypropyl methylcellulose, hydroxypropyl ethylcellulose, sodium carboxymethylcellulose, polyvinyl alcohol, polyvinylpyrrolidone, polyethylene glycol, poly(methyl methacrylate), polycarbophil, gelatin, alginate, poly(acrylic acid), polyethylene oxide, chitosan, derivatives thereof, and mixtures thereof.

14. The method according to claim 12, wherein the chelating agent is a disodium salt of EDTA.

15. The method according to claim 12, wherein the stabilizing agent is selected from the group consisting of sodium hydrogen sulfite, glycerin, sodium citrate, butyl hydroxyanisole, benzalkonium chloride, edetic acid and pharmaceutically acceptable salts thereof, tocopherol, derivatives thereof, and mixtures thereof, alone or in combination with sodium edetate.

16. The method according to claim 12, wherein the isotonizing agent is selected from the group consisting of sodium chloride, potassium chloride, D-mannitol, glucose, glycerin, xylitol, propylene, and mixtures thereof.

17. The method according to claim 12, wherein the thickening agent is selected from the group consisting of methylcellulose, ethyl cellulose, hydroxypropyl methylcellulose, polyvinyl pyrrolidone, polyvinyl alcohol, sodium chondroitin sulfate, sodium hyaluronate, chitosan, and mixtures thereof.

18. The method according to claim 12, wherein the preservative is selected from the group consisting of sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol, and mixtures thereof.

19. The method according to claim 12, wherein the buffering agent comprises a base selected from the group consisting of sodium carbonate, sodium tetraborate, sodium phosphate, sodium acetate, sodium bicarbonate, and mixtures thereof.

20. The method according to claim 12, wherein the electrolyte is sodium chloride or potassium chloride.

21. The method of treating nasal allergic conditions according to claim 1, wherein said nasal allergic condition is allergic rhinitis.

22. The method of treating nasal allergic conditions according to claim 1, wherein said nasal allergic condition is asthma.

23. The method of claim 21, wherein said patient is an animal or a human.

24. The method of claim 22, wherein said patient is an animal or a human.

\* \* \* \* \*